(12) United States Patent
Abedini et al.

(10) Patent No.: US 9,980,649 B1
(45) Date of Patent: May 29, 2018

(54) SKIN SCANNING DEVICE WITH HAIR ORIENTATION AND VIEW ANGLE CHANGES

(71) Applicant: INTERNATIONAL BUSINESS MACHINES CORPORATION, Armonk, NY (US)

(72) Inventors: Mani Abedini, Pascoe Vale (AU); Rajib Chakravorty, Epping (AU); Rahil Garnavi, Macleod (AU); Lenin Mehedy, Doncaster East (AU)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/433,588

(22) Filed: Feb. 15, 2017

(51) Int. Cl.
*A61B 5/00* (2006.01)
*H04N 5/232* (2006.01)
*H04N 7/18* (2006.01)
*H04N 5/225* (2006.01)
*A61B 90/35* (2016.01)
*A61B 90/50* (2016.01)
*A61B 34/30* (2016.01)

(52) U.S. Cl.
CPC .......... *A61B 5/0064* (2013.01); *A61B 5/0077* (2013.01); *A61B 5/441* (2013.01); *A61B 5/70* (2013.01); *A61B 34/30* (2016.02); *A61B 90/35* (2016.02); *A61B 90/50* (2016.02); *H04N 5/2256* (2013.01); *H04N 5/23203* (2013.01); *H04N 7/181* (2013.01); *A61B 2562/0233* (2013.01)

(58) Field of Classification Search
None
See application file for complete search history.

(56) References Cited

U.S. PATENT DOCUMENTS

| | | | |
|---|---|---|---|
| 5,957,090 A * | 9/1999 | Larson | A01K 13/002 119/600 |
| 2007/0106306 A1* | 5/2007 | Bodduluri | A61B 17/32053 606/133 |
| 2009/0052738 A1 | 2/2009 | Qureshi et al. | |
| 2009/0118600 A1* | 5/2009 | Ortiz | A61B 5/0064 600/306 |
| 2009/0318815 A1* | 12/2009 | Barnes | A61B 5/0062 600/473 |
| 2011/0040192 A1* | 2/2011 | Brenner | A61B 5/0059 600/476 |
| 2012/0206587 A1* | 8/2012 | Oz | A61B 5/0064 348/77 |

OTHER PUBLICATIONS

Beeler, T. et al., "Coupled 3D Reconstruction of Sparse Facial Hair and Skin" ACM Transactions on Graphics (Jul. 2012) pp. 117:1-117:10, vol. 31, No. 4, Article 117.

* cited by examiner

*Primary Examiner* — W B Perkey
(74) *Attorney, Agent, or Firm* — Tutunjian & Bitetto, P.C.

(57) ABSTRACT

A scan head for scanning skin includes a frame and a camera coupled to the frame. A controllable probe is coupled to the frame and is configured to change an orientation of hair on the skin to be examined and imaged with the camera.

20 Claims, 6 Drawing Sheets

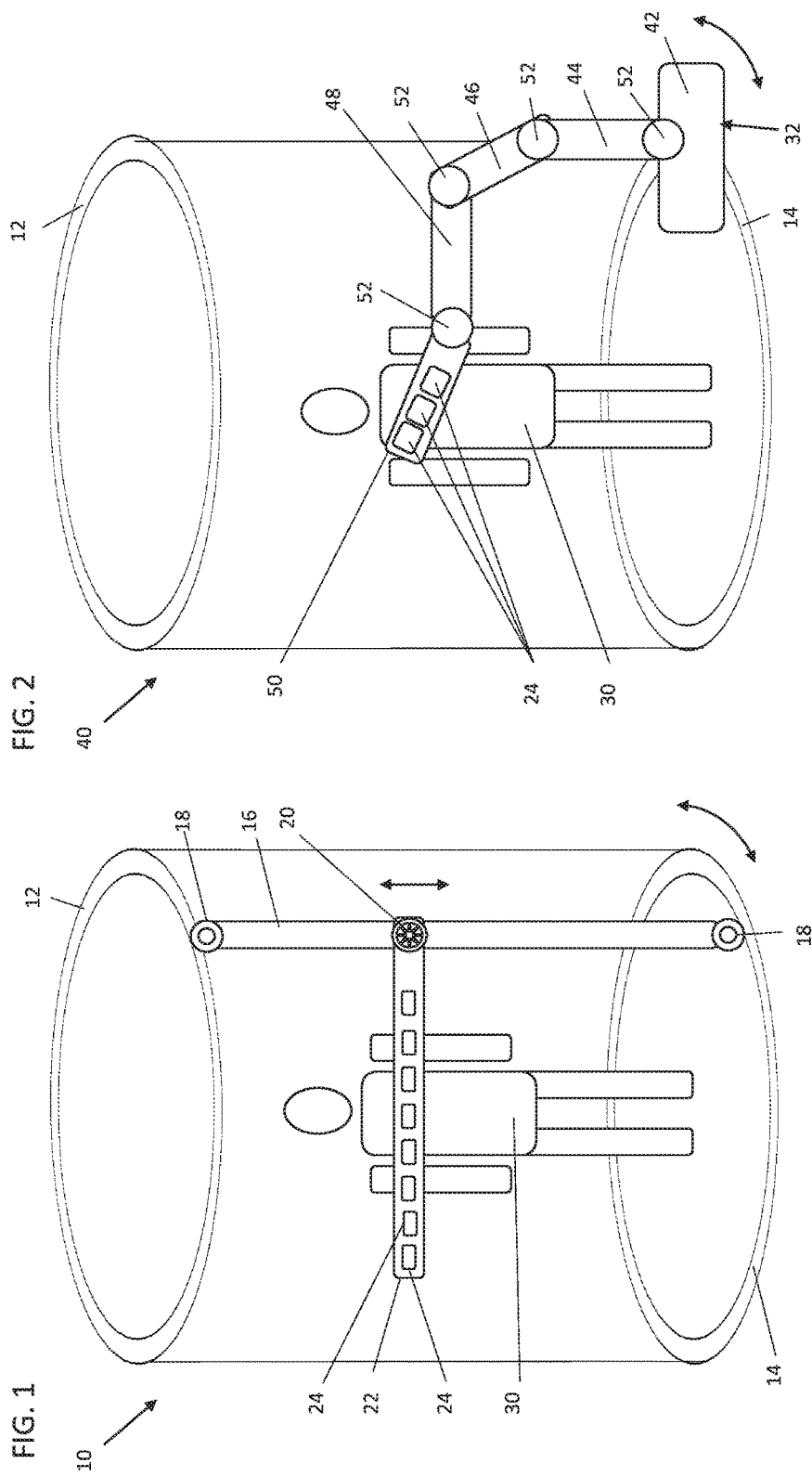

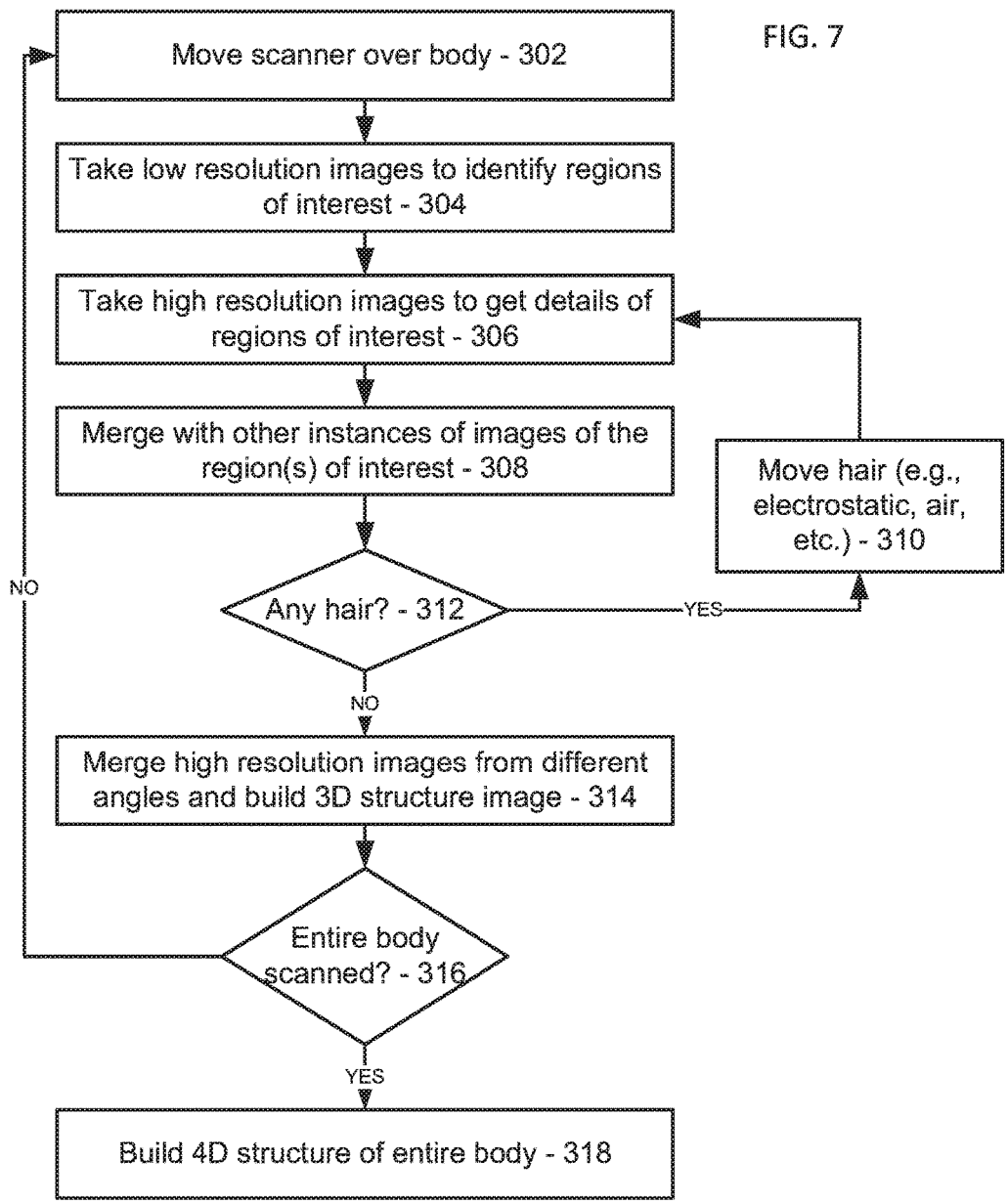

SKIN SCANNING DEVICE WITH HAIR ORIENTATION AND VIEW ANGLE CHANGES

BACKGROUND

Technical Field

The present invention generally relates to full-body scanning, and more particularly to systems, methods and devices for skin scans that alter hair orientation and view angles to provide a more complete scan dataset.

Description of the Related Art

To determine the health and well-being of an individual both internally and externally the body can be examined by a physician using a plurality of tools. For internal examinations, imaging tools can employ technologies, such as, fluoroscopy, computed tomography, ultrasound, magnetic resonance, etc. These technologies are aided by computer-based image filtering and magnification. External examinations are generally performed using the human eye to detect skin abnormalities, and while magnification can be employed, the external exam is typically based on the vision of the examiner.

Scanning for various skin diseases such as Melanoma can be performed using scanners. However, existing scanners may not able to capture sufficient detailed information to make a proper diagnosis.

SUMMARY

In accordance with an embodiment of the present invention, a scan head for scanning skin includes a frame and a camera coupled to the frame. A controllable probe is coupled to the frame and is configured to change an orientation of hair on the skin to be examined and imaged with the camera.

A scanning system includes a link having one or more scan heads formed thereon and a robot coupled to the link and configured to scan the link over skin of a body. The one or more scan heads include a frame, at least one camera coupled to the frame and a controllable probe coupled to the frame and configured to change an orientation of hair on the skin to be examined and imaged with the at least one camera.

A method for scanning skin includes scanning skin using a scan head having at least one camera coupled to a frame and a controllable probe coupled to the frame; activating the controllable probe to change an orientation of hair on the skin to be examined; and imaging an area of interest with the orientation of hair changed using the at least one camera.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 1 is a schematic diagram showing robot shafts for conveying a link with image capture probes (scan heads) in accordance with an embodiment of the present invention;

FIG. 2 is a schematic diagram showing a robot mechanism for conveying a link with image capture probes (scan heads) in accordance with an embodiment of the present invention;

FIG. 7 is a block/flow diagram showing a system/method for scanning skin in accordance with another embodiment of the present invention.

DETAILED DESCRIPTION

Figure 3:
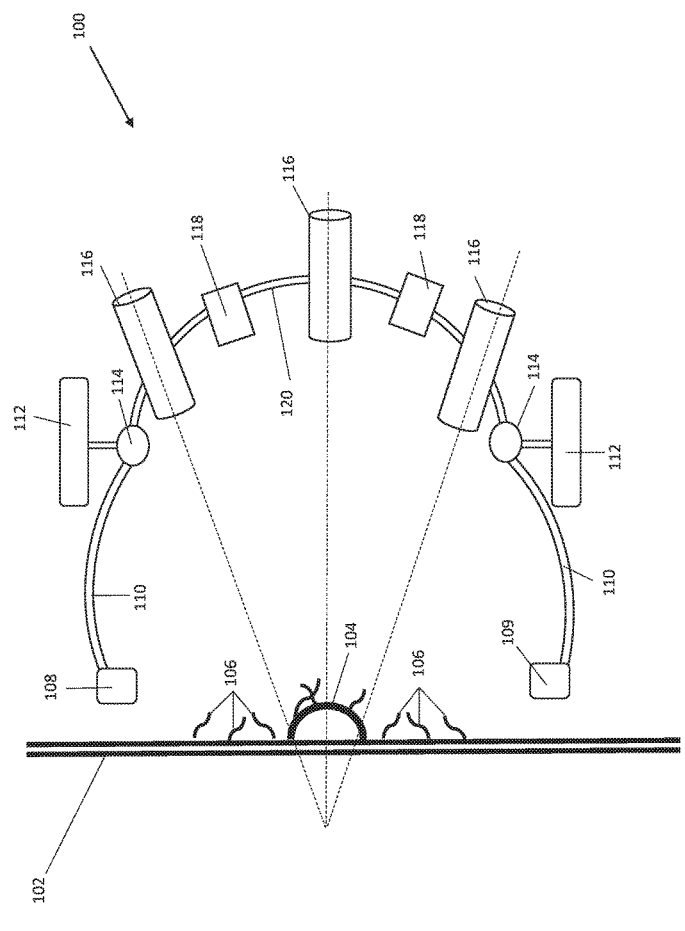
FIG. 3 is a schematic diagram showing a scan head with probes, cameras and lights in accordance with an embodiment of the present invention.

In accordance with embodiments of the present invention, scanning systems, devices and methods are provided that increase the amount of detail measured by a scan. The present embodiments can include a robot arm, robot shaft, robot system or other mechanism (referred to herein as a robot) to automatically scan the body of a patient. The robot includes a scan head configured with electrostatic probes, light sources, cameras, sensors, etc. to observe, measure, image and otherwise capture details of the skin surface. In other embodiments, the scan head can be wielded manually.

In useful embodiments, light sources can produce light spectra including one or more of visible, infrared, ultraviolet, x-ray, etc. Cameras employed herein can be conventional image capture devices or any other type of image sensor that can capture images not only in the visible light spectrum but also in other wavelength spectrum, such as, e.g., ultraviolet, infrared, etc. Sensors can include humidity sensors, temperature sensors, proximity sensors, positional sensors, etc.

The scan head is repositionable about a single focus point so that a given skin position can be observed and photographed at a plurality of angles. The electrostatic probes can be distributed on the scan head to electrostatically reorient hair on the skin to better observe the underlying conditions. The hair may be reoriented a number of times at a same camera angle to find a best observation scenario. Other ways of reorienting hair can include air fans or blowers, brushes, etc.

The lights, cameras and other features on the scan head can be repositioned using motors or other mechanisms to alter the configuration to better collect observation data from a given location. Multiple image sensors and associated lighting sources can be synchronized (e.g., turned on and off) in a manner to take images of a focused skin area with different illumination and shadow conditions such that external growth can be measured or conditions observed.

The present embodiments can be employed in a number of useful applications including medical applications, e.g., scanning for Melanoma or other skin diseases; can be employed for cosmetic applications, e.g., evaluating skin conditions for selection of moisturizes, make-up types, etc.

In one embodiment, a full body scanner is employed that includes one or more robotic shafts/arms carrying one or more scanner heads. The scanner heads each include one or more image capture devices and electrostatic charge probes. In one embodiment, one or more small hair displacement devices, e.g., electrostatic charge probes, fans, vacuum or air suction device, etc., can be mounted on electronically controllable robotic arms and used to move skin hairs in different directions such that pictures of a skin location can be taken with skin hairs in different but controlled orientations. The image sensors and associated lighting sources can be arranged in a curved (e.g., concave) electronically controllable vertical shaft to take pictures of a focused skin location from different angles concurrently. The multiple image sensors and associated lighting sources can be synchronized to take pictures of the focused skin area with different illumination and shadow conditions to correctly measure the external growth, etc. of that area without repositioning the scan head, although the scan head can be repositioned for the different conditions. The robot or electronically controllable shaft can be moved vertically and horizontally (or circularly) to adjust to an appropriate distance from the skin for better focus and effective capturing of skin images.

It is to be understood that aspects of the present invention will be described in terms of a given illustrative architecture; however, other architectures, structures, materials, process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

It should also be understood that material compounds will be described in terms of listed elements. These compounds can include different proportions of the elements within the compound. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a body scan configuration 10 is illustratively shown in accordance with one embodiment. The configuration 10 provides a full or partial body scanner that can be controlled using two shafts 16 and 22. One shaft 22 includes image capture probes 24 that can be moved vertically (e.g., up-down) along the second shaft 22. The first shaft 16 and the second shaft 22 can be connected using a wheel 20 or other sliding connection. The first shaft 16 and the second shaft 22 are robot shafts that can be controlled using a manual controller or automatically controlled using a computer and control software.

The probes 24 can include an entire scanner head, one or more sensors, or combinations of different features or probes. Another shaft 16 can be moved in a circular path on wheels 18 around a body 30. The wheels 18 can be run on rails 12, 14. In this architecture, only a subset of sensors that overlap the body area are activated to take pictures of the skin. With the degrees of freedom afforded by the two shafts 16, 22 and the placement and design of the probes 24, every location on the body 30 can be scanned. In other embodiments, preprogrammed portions of the body 30 can be scanned without doing an entire body scan.

Referring to FIG. 2, an alternative body scan configuration 40 is illustratively shown in accordance with another embodiment. The configuration 40 includes a robot 32 having a base 42 moveable along a track 14 or predetermined pattern. The robot 32 can include one or more linkages 44, 46, 48, 50 with universal joints 52 or other joints 52 therebetween. A robotic arm or linkage 50 can include image capture sensors 24, which are mounted on the arm 50 and have many degrees of freedom to enable full coverage or partial coverage of a body scan. The arm 50 can be waved about the body 30 to scan the skin, capture images and store observations.

A controlling program or algorithm stored in a computer or console (not shown) can be programmed to move the shafts 16, 22 (FIG. 1) or arm 50 (FIG. 2), as appropriate, depending on a region of interest or type of analysis to be performed. For example, a first scan may be an exhaustive scan with many images taken of every part of the skin of the body 30. The first scan may be a base or reference scan. Later, a new scan may take pictures selectively at one or more regions of interest (e.g., moles, etc.) found in the first scan.

It should be understood that other scan configurations are contemplated. For example, the patient may be prone instead of vertical, the scanning mechanism may include a spherical system instead or cylindrical, etc. Other robots, mechanisms and even manual scanning may be employed.

Referring to FIG. 3, a scan head 100 is illustratively shown in accordance with one embodiment. Scan head 100 includes a frame 120 that can be shaped in any useful arrangement. Scan head 100 depicts an arcuate shaped frame 120 although the frame 120 can be semicircular, semi-oval, a line, a polygonal shape, etc. In one embodiment, the frame 120 includes joints with a controller (e.g., stepper motors or actuators) 114 secured thereon. The controllers 114 can include a servo, motor or other actuator that is capable of moving, adjusting or otherwise controllably positioning probe holders 110. The frame 120 is secured to a robot arm or shaft with one or more holder shafts 112. The holder shafts 112 provide a stable connection to the robot to enable the positioning of the frame 120 relative to skin 102 or other surface.

The probe holders 110 include probes 108, 109 at a distal end portion. The probes 108, 109 can be repositioned in accordance with the controller 114. In one embodiment, the probes 108, 109 can include electrostatic probes for displacing hair. The electrostatic probes 108, 109 can be configured to build up static electric charge to reorient hairs 106 on the skin 102. In other embodiments, the probes 108, 109 can include air movement or pressure altering devices, e.g., air puffers, fans, vacuum or air suction devices, for displacing hair. In still other embodiments, the probes 108, 109 can include mechanical devices, such as brushes, tweezers, mechanical probes, etc. for displacing hair. During a scanning operation, the probes 108, 109 can be repositioned to reorient the hairs to provide a better viewing of an area of interest 104, e.g., a mole, lesion or other blemish.

The frame 120 can further support a number of other features for measuring, observing or recording information about the area of interest 104 or skin 102, in general. In useful embodiments, the frame 120 includes light sources 118, cameras or sensors 116, or other devices. The cameras 116 can include fiber optics, imaging chips, CCD cameras, or any other optical capture device. The lights 118 can be light emitting diodes (LEDs), incandescent bulbs, or any other useful light source. The light sources 118, cameras or sensors 116 can be configurable and controllable to change their orientation angle in any direction about the frame 120.

In accordance with a particularly useful embodiment, the scan head 100 has multiple image sensors 116 mounted on the frame (e.g., a concave shaft) such that the sensors 116 have a common focal point on the skin 102 (e.g., area of interest 104) and are able to take images of the focal point from different angles. Similarly, lighting sources 118 are arranged to provide light to the focal point at different angles to provide complete lighting. Lighting sources 118 can be placed in between the cameras 116 with the same focal point such that the lighting sources 118 can illuminate the focal point on the skin 102 from different angles.

Figure 4:
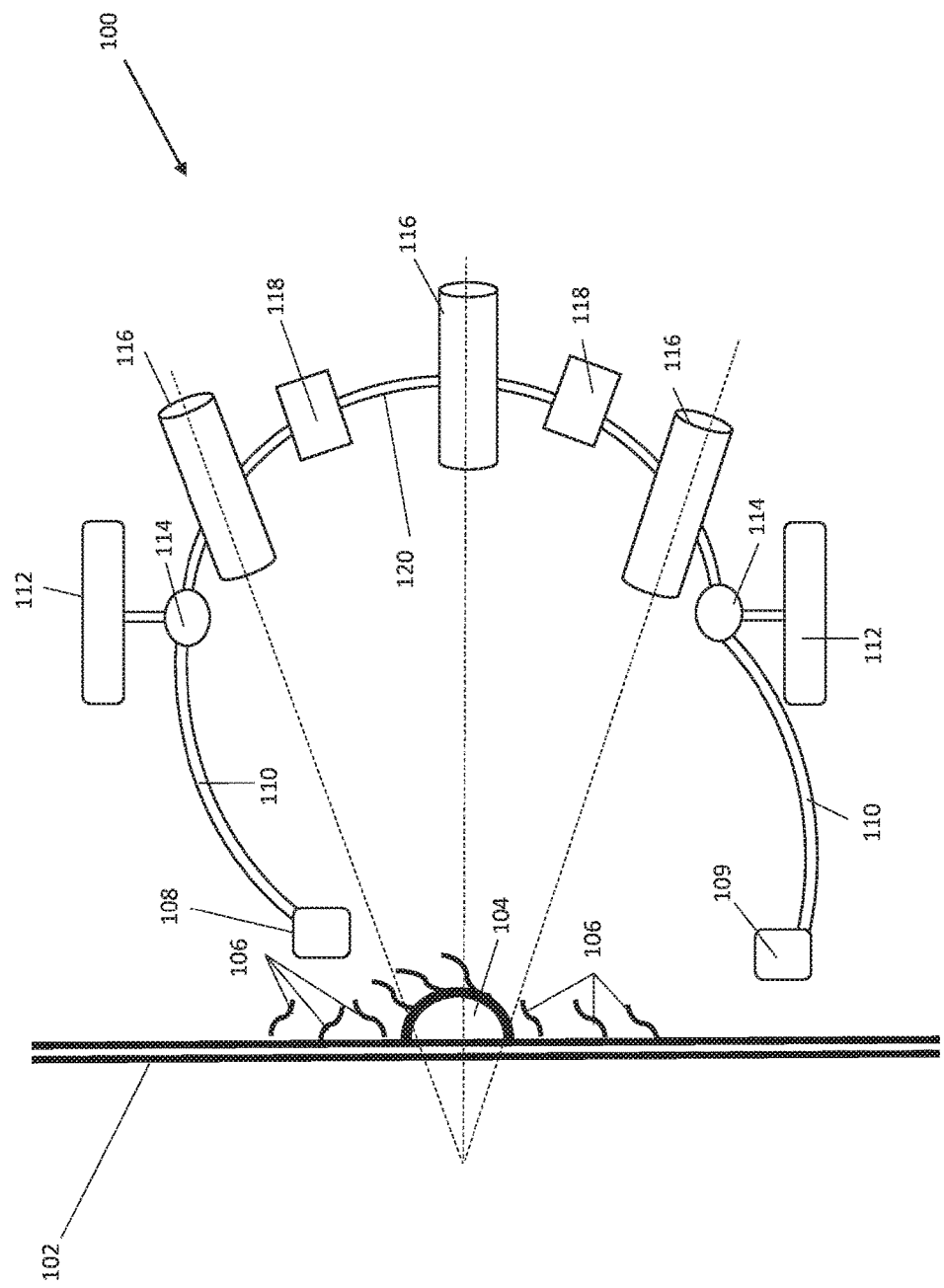
FIG. 4 is a schematic diagram showing a scan head with a first probe moved and activated in accordance with an embodiment of the present invention.
Figure 5:
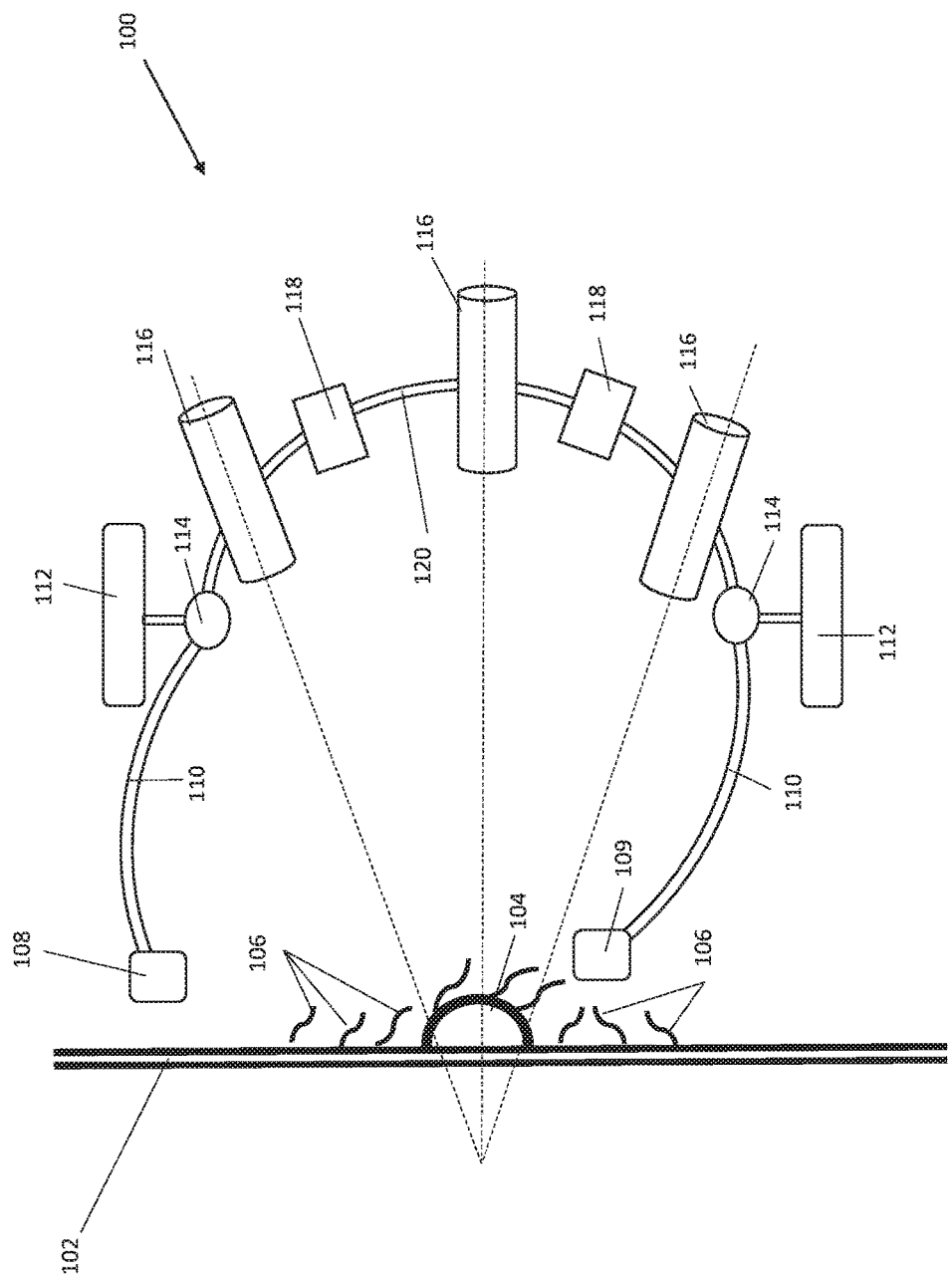
FIG. 5 is a schematic diagram showing the scan head of FIG. 4 with a second probe located at a different position than the first probe and activated in accordance with an embodiment of the present invention.

Referring to FIGS. 4 and 5, the scan head 100 is depicted at different points in a scan procedure to demonstrate the use of the probes 108, 109 to improve image capture and preserve details. In FIG. 4, the scan head 100 is passed in proximity to the skin 102 and the area of interest 104. The controller arms or probe holders 110 with electrostatic probes 108, 109 are moved to permit one probe 108 to move closer to the area of interest 104 close to the focal point on the skin 102, as needed. The static charge of probe 108 (with probe 108 turned on and probe 109 turned off) causes the hair 106 to move in a first direction (toward the probe 108). The controller arms 110 can be manipulated to move the hair 106 out of the way of the camera perspective. The controller arms 110 can be controlled using controllers 114 at a base of the arms joining the frame 120.

In FIG. 5, the controller arms or probe holders 110 with electrostatic probes 108, 109 are moved again to permit one probe 109 to move closer to the area of interest 104 close to the focal point on the skin 102, from a different direction, as needed. The static charge of probe 109 (with probe 108 turned off and probe 109 turned on) causes the hair 106 to move in a second direction (toward the probe 109). The controller arms 110 can be manipulated to move the hair 106 out of the way of the camera perspective to ensure that the area of interest is further analyzed from different perspectives. The controller arms 110 can be controlled using stepper motors at a base of the arms joining the frame 120.

It should be understood that the whole scan head 100 can be rotated in any direction (including about the focal point) and can be rotated around multiple axes/pivots (e.g., x and y) for capturing images at the focal point (or around the focal point) for all possible angles of view, if needed. Alternatively, the robot shafts or arms can move to provide the same function. Images are captured at different angles and with hairs 106 at different orientations.

Figure 6:
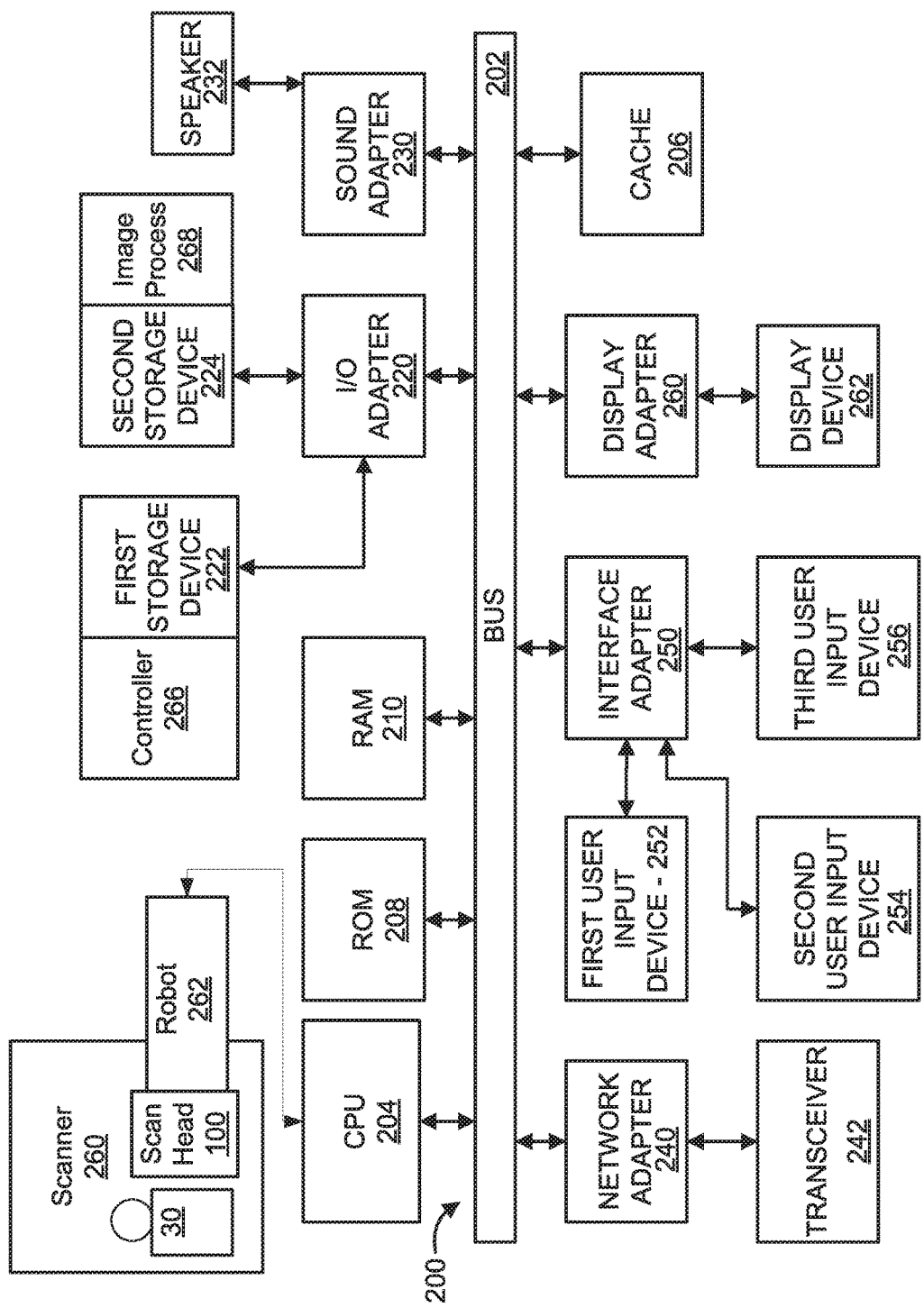
FIG. 6 is a block/flow diagram showing a system for scanning skin in accordance with one embodiment of the present invention.

Referring to FIG. 6, an exemplary processing system 200 to which the present invention may be applied is shown in accordance with one embodiment. The processing system 200 includes at least one processor (CPU) 204 operatively coupled to other components via a system bus 202. A cache 206, a Read Only Memory (ROM) 208, a Random Access Memory (RAM) 210, an input/output (I/0) adapter 220, a sound adapter 230, a network adapter 240, a user interface adapter 250, and a display adapter 260, are operatively coupled to the system bus 202.

A first storage device 222 and a second storage device 224 are operatively coupled to system bus 202 by the I/0 adapter 220. The storage devices 222 and 224 can be any of a disk storage device (e.g., a magnetic or optical disk storage device), a solid state magnetic device, and so forth. The storage devices 222 and 224 can be the same type of storage device or different types of storage devices.

A speaker 232 is operatively coupled to system bus 202 by the sound adapter 230. A transceiver 242 is operatively coupled to system bus 202 by network adapter 240. A display device 262 is operatively coupled to system bus 202 by display adapter 260.

A first user input device 252, a second user input device 254, and a third user input device 256 are operatively coupled to system bus 202 by user interface adapter 250. The user input devices 252, 254, and 256 can be any of a keyboard, a mouse, a keypad, an image capture device, a motion sensing device, a sensor, a microphone, a device incorporating the functionality of at least two of the preceding devices, and so forth. Of course, other types of input devices can also be used, while maintaining the spirit of the present invention. The user input devices 252, 254, and 256 can be the same type of user input device or different types of user input devices. The user input devices 252, 254, and 256 are used to input and output information to and from system 200.

Of course, the processing system 200 may also include other elements (not shown), as readily contemplated by one of skill in the art, as well as omit certain elements. For example, various other input devices and/or output devices can be included in processing system 200, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 200 are readily contemplated by one of ordinary skill in the art given the teachings of the present invention provided herein.

The system 200 includes a scanner 260, such as a full body scanner with a robot 262 or other mechanism. A patient stands in a housing of the scanner 260 with exposed skin areas. A controller module 266 stored in memory (e.g., the first storage device 222 or second storage device 224) can include a program or algorithm that resets and adjusts a shaft or shafts of the robot 262 close enough to the body. Then, a scan head 100 coupled to the robot 262 can start to capture images of the body 30.

After each full-scan around the body at a certain height, the scan head 100 moves and continues to scan different areas until a full (or partial) body scan is complete. The controller module 266 can be programmed to control the robot to cover any portion of the body by controlling the positions permitted for the robot 262 and scan head 100. Image capture can be performed at any and all locations or a certain location(s) on the body in particular using different settings in the controller module 266. In one example, images can be taken with different illuminations and shadows. Different coordinated sequences can be executed to obtain more details in the skin scan. For example, one sequence can include turning electrostatic probes OFF, and one or more lights ON to capture an image, then, change the order or number of lights ON with the electrostatic probes still OFF.

Images can be captured with body-hair in different orientations, e.g., one electrostatic probe is ON and close to the focal area to attract the hairs in one direction and one or more lights are ON. Then, alternative lights can be turned ON. Different light settings can also be used that will permit shadow capture of the hairs and facilitate image processing. Then, images can be taken with a different probe ON (and the first probe OFF) as well as with different illumination settings (lights ON or OFF). The lights, cameras, probes, etc. can all be adjusted using the controller module 266. The system 200 can also take images selectively for the locations that may be interesting (e.g., having moles), or a full scan of every part of the skin for a base reference.

An image processing module 268 stored in memory (e.g., the first storage device 222 or second storage device 224) can be employed to determine whether hair is present using image detection software. The image processing module 268 can also be employed to stitch or merge together multiple images to form a model or complete scan image.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring to FIG. 7, methods for skin scanning are illustratively shown. In block 302, a scan head is moved over skin areas of a body to be examined. The scan head can be coupled to a robot or other mechanism to controllably scan over different areas of the body or to do a complete full body scan. In block 304, images are taken over the body. In one embodiment the initial scanning includes low resolution images to identify areas where further scanning and details are needed. In block 306, high resolution images are taken of lesions or other areas of interest. In block 308, images are merged for a particular area of interest. This can include different angles of the same spot, different lighting conditions, different camera angles, etc.

In block 312, a determination is made as to whether any hair is present in the images. This can be performed using image processing software that can identify hair in the images. In block 310, if hair is present, the scan head moves the hair using electrostatic charge, brushing, an air puffer, etc. and returns to block 306 to take high resolution images with the hair in a different orientation.

In block 314, the high resolution images can be merged to develop or build a three dimensional image structure. In block 316, a determination is made as to whether an entire scan is provided (or all designated area of interest have been scanned). If the entire area is not scanned, the path returns to block 302, otherwise, a four-dimensional (4-D) structure of the entire body or portion thereof is constructed. 4-D refers to volume (x, y, z) and time (t).

Having described preferred embodiments for a skin scanning device with hair orientation and view angle changes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A scan head for scanning skin, comprising:
a frame;
at least one camera coupled to the frame;
a controller secured to the frame, the controller having an elongated controller arm coupled thereto; and
a controllable probe coupled to the elongated controller arm, the controller configured to move the elongated controller arm to reposition the controllable probe relative to the frame, said controllable probe being configured to change an orientation of hair on the skin to be examined and imaged with the at least one camera.

2. The scan head as recited in claim 1, wherein the controllable probe includes an electrostatic probe that changes the orientation of hair using static charge.

3. The scan head as recited in claim 1, wherein the controllable probe includes an air puffer probe that changes the orientation of hair using air movement.

4. The scan head as recited in claim 1, further comprising lights coupled to the frame to illuminate an area of interest.

5. The scan head as recited in claim 4, wherein the lights are interspersed on the frame between the at least one camera.

6. The scan head as recited in claim 1, wherein the controllable probe is coupled to a distal end of the elongated controller arm.

7. The scan head as recited in claim 1, wherein the frame is coupled to a robot system wherein the robot system provide controlled movement of the scan head.

8. A scanning system, comprising:
- a link having one or more scan heads formed thereon;
- a robot coupled to the link and configured to scan the link over skin of a body;
- the one or more scan heads including:
- a frame;
- at least one camera coupled to the frame;
- a controller secured to the frame, the controller having an elongated controller arm coupled thereto; and
- a controllable probe coupled to the elongated controller arm, the controller configured to move the elongated controller arm to reposition the controllable probe relative to the frame, said controllable probe being configured to change an orientation of hair on the skin to be examined and imaged with the at least one camera.

9. The scan head as recited in claim 8, wherein the controllable probe includes an electrostatic probe that changes the orientation of hair using static charge.

10. The scan head as recited in claim 9, wherein the controllable probe includes an air puffer probe that changes the orientation of hair using air movement.

11. The scan head as recited in claim 8, further comprising lights coupled to the frame to illuminate an area of interest.

12. The scan head as recited in claim 11, wherein the lights are interspersed on the frame between the at least one camera.

13. The scan head as recited in claim 8, wherein the controllable probe is coupled to a distal end of the elongated controller arm.

14. The scan head as recited in claim 8, wherein the robot is controlled by a control module to provide controlled movement of the one or more scan heads.

15. A method for scanning skin, comprising:
- scanning skin using a scan head having at least one camera and a controller coupled to a frame, an elongated controller arm coupled to the controller and a controllable probe coupled to the elongated controller arm, the controller configured to move the elongated controller arm to reposition the controllable probe relative to the frame;
- activating the controllable probe and repositioning the controllable probe relative to the frame to change an orientation of hair on the skin to be examined;
- imaging in area of interest with the orientation of hair changed using the at least one camera.

16. The method as recited in claim 15, wherein the controllable probe includes an electrostatic probe and activating the controllable probe includes changing the orientation of hair using static charge.

17. The method as recited in claim 15, wherein the controllable probe includes an air puffer and activating the controllable probe includes changing the orientation of hair using air movement.

18. The method as recited in claim 15, further comprising lights coupled to the frame and further comprising illuminating an area of interest with the lights.

19. The method as recited in claim 15, wherein the controllable probe is coupled to a distal end of the elongated controller arm.

20. The method as recited in claim 15, wherein the robot provides controlled movement of the scan head.

* * * * *